United States Patent [19]
Matturro et al.

[11] Patent Number: 5,162,599
[45] Date of Patent: Nov. 10, 1992

[54] RAPID THERMAL PYROLYSIS OF GASEOUS FEEDS CONTAINING HYDROCARBON MOLECULES MIXED WITH AN INERT WORKING GAS

[75] Inventors: Michael G. Matturro, Lambertville; Harry W. Deckman, Clinton; Frank Hershkowitz, Liberty Corner; Anthony M. Dean, Hampton, all of N.J.

[73] Assignee: Exxon Research and Engineering Co., Florham Park, N.J.

[21] Appl. No.: 762,189

[22] Filed: Sep. 19, 1991

[51] Int. Cl.⁵ .............................................. C07C 2/00
[52] U.S. Cl. .................................... 585/943; 585/402; 585/500; 585/503; 585/700; 585/910
[58] Field of Search ............... 585/943, 402, 500, 503, 585/700, 910

[56] References Cited

U.S. PATENT DOCUMENTS

| | | | |
|---|---|---|---|
| 4,672,144 | 6/1987 | Green | 585/943 |
| 4,724,272 | 2/1988 | Ranisre et al. | 585/943 |
| 4,926,001 | 5/1990 | Alagy et al. | 585/943 |
| 4,929,797 | 5/1990 | Yamaguchi et al. | 585/943 |

Primary Examiner—Asok Pal
Attorney, Agent, or Firm—Joseph J. Dvorak

[57] ABSTRACT

In its simplest sense, the present invention is directed toward a process for the thermal conversion of methane into unsaturated gaseous hydrocarbons, especially olefins, comprising first compressing methane in the presence of an inert gas having a higher ratio of heat capacities, $C_p/C_v$, than methane. The inert gas used is present in an amount sufficient to provide a compressed gas mixture having a peak temperature of adiabatic compression in the range of about 900° C. to about 2200° C. Under these conditions, at least some of the methane is converted to unsaturated gaseous hydrocarbons. Immediately thereafter, the compressed gas mixture is expanded, thereby substantially preventing thermal conversion of the gaseous hydrocarbons. Importantly, the compression and expansion are achieved in a single cycle of less than about one second.

10 Claims, 3 Drawing Sheets

RAPID THERMAL PYROLYSIS OF GASEOUS FEEDS CONTAINING HYDROCARBON MOLECULES MIXED WITH AN INERT WORKING GAS

FIELD OF THE INVENTION

This invention relates to the conversion of methane to more useful products, such as ethylene and the like. More particularly, the present invention relates to the rapid, gas phase conversion of methane, under high temperature and pressure conditions, to higher molecular weight, unsaturated hydrocarbons and hydrogen.

BACKGROUND OF THE INVENTION

It has been suggested to carry out chemical reactions under high pressure and temperature conditions by compressing a reactant gas under conditions approaching adiabatic until the desired temperature and pressure is obtained, and then subsequently cooling the reaction products as rapidly and as adiabatically as practical. Indeed, in U.S. Pat. No. 2,814,551, there is disclosed a reactor having a cylinder equipped with a reciprocating piston for subjecting a gaseous reactant fed to the cylinder to high temperature conditions for a short time.

In U.S. Pat. No. 4,265,732, three types of chemical reactors are disclosed for the non-catalytic cracking of hydrocarbons, such as ethane, propane and the like, and high temperatures and pressures to produce lower molecular weight hydrocarbons. Among the types of reactors presented are positive displacement type machines similar to conventional four-stroke engines, compressor/turbine axial type reactors and energy dissipator axial type reactors.

While the just-mentioned references demonstrate that some success has been met in thermally cracking larger molecules to smaller molecules, there appear to be scant reports dealing with the commercially practical formation of larger molecules, such as olefins, from a smaller molecule, such as methane, by means of rapid adiabatic compression.

In *Dokl. Akad. Nauk SSR*, 40, pp. 1376-1379 (1961), methane is reported to be converted to acetylene after rapid compression to elevated temperatures and pressures, essentially in a shock tube type reactor.

Accordingly, it is an object of the present invention to provide a method for converting methane to hydrogen and light gaseous hydrocarbons, such as unsaturated hydrocarbons, including ethylene, acetylene, propylene and the like.

SUMMARY OF THE INVENTION

In its simplest sense, the present invention is directed toward a process for the thermal conversion of methane into unsaturated gaseous hydrocarbons, especially olefins, comprising first compressing methane in the presence of an inert gas having a higher ratio of heat capacities, $C_p/C_v$, than methane. The inert gas used is present in an amount sufficient to provide a compressed gas mixture having a peak temperature of adiabatic compression in the range of about 900° C. to about 2200° C. Under these conditions, at least some of the methane is converted to unsaturated gaseous hydrocarbons. Immediately thereafter, the compressed gas mixture is expanded, thereby substantially preventing thermal conversion of the gaseous hydrocarbons. Importantly, the compression and expansion are achieved in a single cycle of less than about one second.

In a particularly preferred embodiment of the present invention, the thermal conversion of methane is achieved continuously in a positive displacement type machine, such as a diesel engine, at rates greater than about 60 compression and expansion cycles per minute.

DETAILED DESCRIPTION OF THE INVENTION

A key feature of the present invention is to initiate the thermal conversion of methane in the gaseous phase to form hydrogen and unsaturated hydrocarbons having molecular weights greater than methane and containing large proportions of olefins, such as ethylene, propylene and then to rapidly expand the hydrocarbons to substantially prevent the thermodynamically less stable hydrocarbon products from decomposing. This requires the thermal conversion, in effect, to be carried out very rapidly; i.e., in a single compression and expansion cycle of less than one second and in the range of about .1 second to about 0.0001 second. This rapid thermal conversion can be conveniently achieved in a positive displacement type engine, such as a diesel engine and, consequently, the invention will be described in particular detail in connection with such an engine, although any reciprocating engine can be employed.

Figure 1:
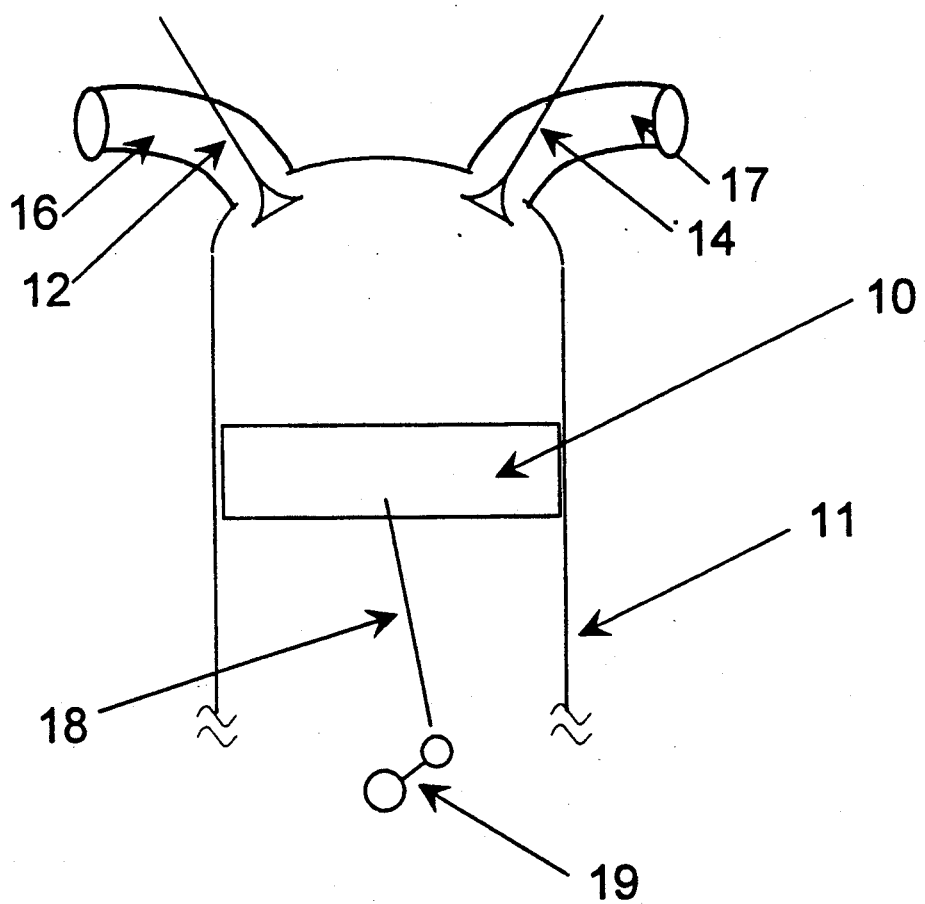
FIG. 1 is a diagrammatic illustration of a single cylinder of a positive displacement type engine.

Turning first to FIG. 1, there is shown a single cylinder of a positive displacement type engine. As should be readily appreciated, a positive displacement type engine, such as a diesel engine, will have a number of cylinders. For convenience, one cylinder is shown in FIG. 1.

As is shown, a piston 10 is located within the cylinder 11. Sealing rings (not shown) are provided to prevent leakage of gas from the cylinder and to insure the compression of the methane containing feed introduced into the cylinder under operating conditions. Two valves 12 and 14 are shown, one for the inlet 16 and the other at the outlet 17. These valves are designed so as to operate sequentially. A normal engine cooling system (not shown) can be employed to adjust cylinder temperature as one of the means of affecting conversion temperature. A connecting rod 18 is connected to a shaft 19 which rotates at a constant angular speed, driving the piston in a reciprocating manner.

All of these features are a subset of the conventional four-stroke engine features known to persons with skill in the art.

Figure 2:
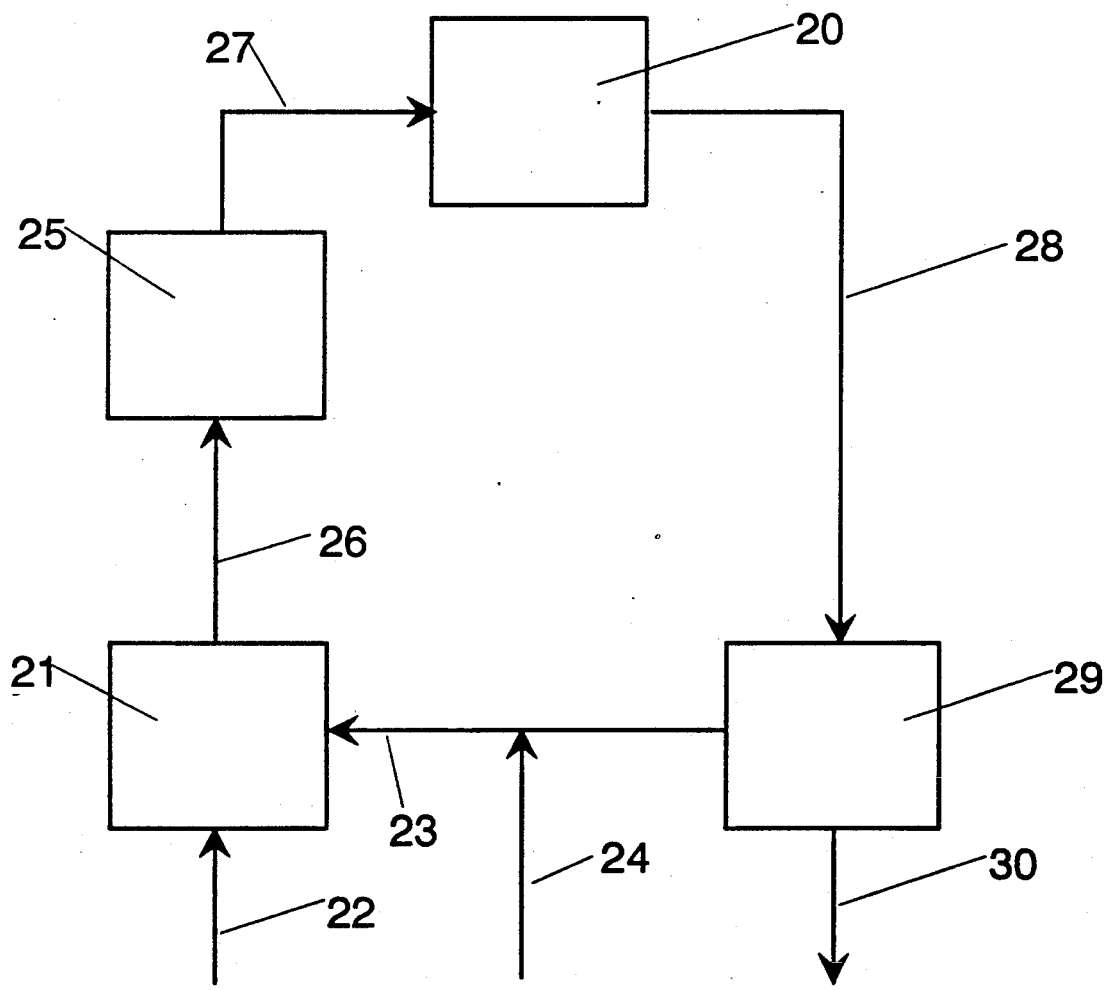
FIG. 2 is a schematic flow diagram showing a preferred operating scheme in accordance with the practice of the present invention.

Referring now to the schematic diagram in FIG. 2, the reactor 20 in which the thermal conversion occurs generally will be a positive displacement engine, as described above in connection with FIG. 1. In the process of the present invention, methane is compressed in reactor 20 in the presence of an inert, i.e., chemically unreactive, gas that has a heat capacity ratio, $C_p/C_v$, which is greater than that of methane. In a particularly preferred embodiment of the present invention, therefore, the methane is first mixed with the inert gas in a mixing zone 21. Thus, a line 22 is provided for introducing methane from a methane source (not shown) into the mixing zone 21. The inert gas is fed into the mixing zone 21 via line 23. The inert gas preferably is recycled, as will be explained subsequently; however, makeup inert gas is supplied from an external source (not shown) via line 24.

The amount of inert gas used should, of course, be sufficient to provide a compressed gas mixture having a temperature of adiabatic compression in the range of about 900° C. to about 3000° C. The temperature of adiabatic compression is the temperature that would be theoretically achieved from the mixture when compressed, in the absence of reaction, treating the gas as ideal, and without heat transfer to the environment. It should be readily appreciated that in order to achieve those temperatures and pressures, the amount of gas chosen will depend on a number of factors, such as the specific inert gas used, the compression ratio selected and the temperature of the methane and inert gas mixture prior to compression. Suffice it to state that in the practice of the present invention, a significant amount of the inert gas must be added to the methane to create the requisite temperature rise needed for rapid pyrolysis of the methane. In general, compression ratios employed will be in the range of 2:1 to 1000:1, with a more preferred range of 5:1 to 50:1.

The inert gas employed in this invention will be selected from inert diatomic or rare gases (Ar, He, $N_2$, etc.) because only diatomic and rare gases have a ratio of heat capacities (Cp/Cv) which is large enough to produce the requisite temperature of adiabatic compression. Rare gases, theoretically, have the largest ratio of heat capacities and produce the largest temperature rise. Diatomic gases which have smaller ratios of heat capacity can be used as diluents, but they are not as preferred as the rare gases. The amount of gas, as indicated before, will depend upon the temperature to be achieved during the compression cycle, as well as whether or not the methane and inert gas mixture is preheated. To illustrate, if the gas mixture to be compressed is at a temperature of about 25° C., approximately 95% by volume argon and 5% methane would be employed; however, as the inlet temperature increases, less working gas will be needed.

In the practice of the present invention, it is particularly preferred to preheat the gas mixture in a preheat stage, such as stage 25, shown in FIG. 2. Thus, the gas mixture is fed to the preheat stage 25 by line 26. In the preheat stage 25, the mixture will be preheated to temperatures in the range of about 100° C. to about 1000° C. and, preferably, at temperatures in the range of about 300° C. to about 700° C. After preheating the mixed gases, they are fed, via line 27, into the reactor 20 for compression. In reactor 20, the gases are rapidly compressed to provide the requisite temperatures in the range of about 900° C. to about 3000° C., with a preferred range of 1200° C. to 2700° C.

After being compressed to achieve the requisite reaction temperature, the methane in the gaseous mixture is rapidly converted to hydrogen and hydrocarbons of higher molecular weight than methane. These hydrocarbons include a large proportion of unsaturated compounds, such as ethylene, acetylene and propylene. Immediately thereafter, the down-stroke of the piston results in expansion of the gas, with the result that the reaction mixture is quenched, preventing decomposition of the higher molecular weight hydrocarbons formed. Thus, engine speed can be used as a method to control residence time at high temperatures. The engine speed should be between 60 and 40,000 rpm, with a preferred speed between 60 and 4000 rpm.

The product gases are removed from reactor 20 through line 28 for recovery. As is shown in FIG. 2, the product gases preferably are sent, via line 28, to a separation stage 29 where the hydrogen and desired hydrocarbons are separated for removal via line 30 and the inert gas and recovered methane, if any, is recycled by transfer to the mixing zone 21.

Figure 3:
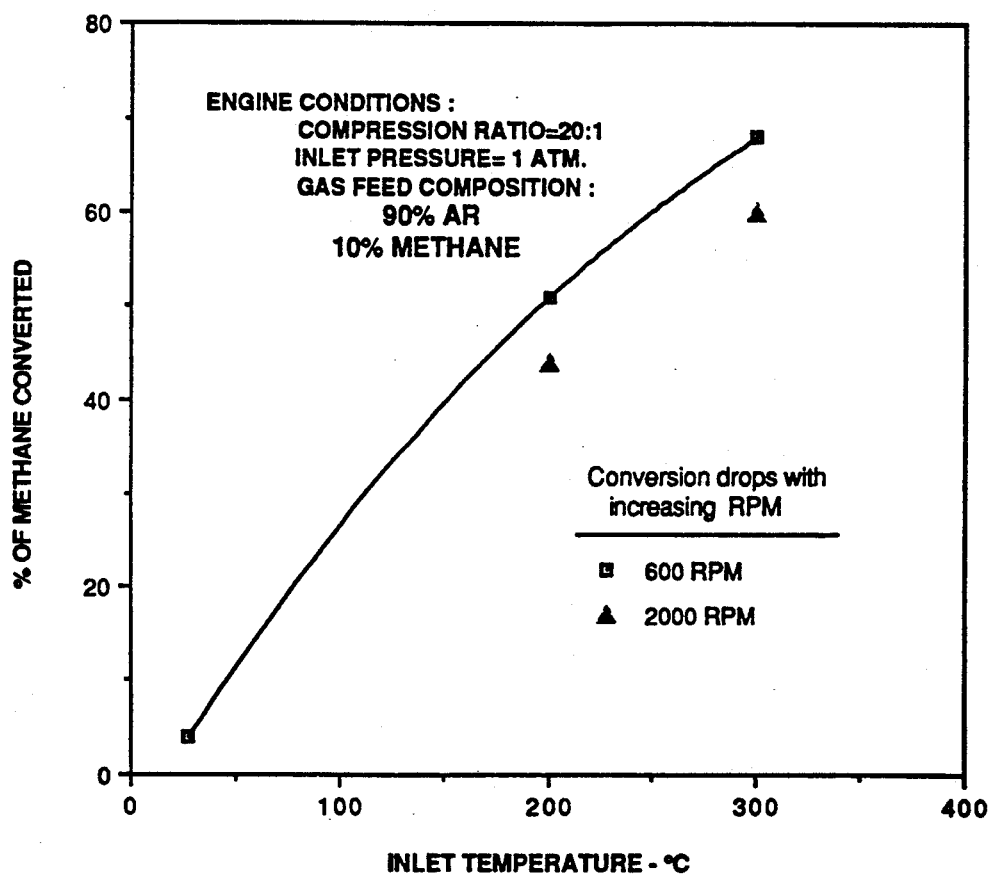
FIG. 3 is a graph showing the inlet temperature dependence on the conversion of methane according to this invention.

As can be seen from FIG. 3, the amount of methane that is thermally converted in a diesel type reactor is a function of inlet temperature and engine rpm. For very dilute gas mixtures, at low conversion levels, the amount of conversion attained is expected to scale linearly with inlet temperature. FIG. 3 shows that the conversion chemistry taking place depends on the available reaction time which, to some degree, is determined by the engine rpm. Also, FIG. 3 shows that at a modest 300° C. inlet temperature, more than 50% of the methane in the gas mixture can be converted to hydrocarbons. If the concentration of methane in the argon is increased from 10 volume percent to 25 volume percent, inlet temperatures greater than about 800° C. will be needed to attain this high level of conversion using the same reaction condition parameters.

As indicated previously, the process of the present invention is capable of producing unsaturated hydrocarbons. Indeed, in accordance with the present invention, ethylene is produced in relatively high yields; e.g., greater than about 10%, based on methane.

EXAMPLES 1 to 8

A series of experiments were conducted using the following general procedure.

(A) General Procedure

A feed gas, containing methane and argon, was supplied from a high pressure cylinder via a high capacity regulator to a preheater and then to the inlet of a reactor engine. The engine used was a single cylinder diesel engine with ~330 cc static displacement capacity. The compression ratio of the engine used was 23 to 1. The engine was powered by an AC motor coupled to the reactor flywheel with a belt drive. The engine temperature was controlled by flowing water through the engine cooling chamber.

Products from reaction within the engine reactor were filtered using 5 and 10 micron stainless steel soot filters, analyzed continuously using a mass spectrometer and fed to a trapp system. Two tube and shell heat exchangers were used as condensors to collect any high molecular weight materials formed. At several points in the reactor system, temperature and pressure was measured using standard thermocouples and gauges.

The reactor also was equipped with a pressure decompression level used to open the exhaust valve during engine startup. This decompression capability was used to conduct control experiments to determine the full effect of piston compression on the chemistry taking place in the engine. After monitoring product composition exiting the reactor under conversion conditions, the decompression valve would be opened to allow measurement of the unreacted feed composition. This technique provided nearly continuous measurement of conversion. The exhaust system was also equipped with a gas handling manifold used to take gas bulb samples for gas chromatographic analysis.

(B) Specific Experiments

The results from eight experiments using 10% (volume) methane in argon are shown below in Table 1. The influence of inlet temperature ($t_i$) on conversion, product selectivity for gaseous hydrocarbon products, total gaseous product recoveries and nonreactive peak temperature of adiabatic compression ($T_{ac}$) is shown.

TABLE 1

Reaction Conditions, Conversions and Product Selectivities
Feed: 10% (vol) Methane, Balance Argon
RPM = 2250
Compression Ratio = 23.1

| Ex. No. | $T_i$ | $T_{ac}$ | Conv | MB | Wt. % Selectivity | | | | | |
|---|---|---|---|---|---|---|---|---|---|---|
| | | | | | $H_2$ | $C_2H_2$ | $C_2H_4$ | $C_2H_6$ | $C_3H_6$ | $C_6H_6$ |
| 1 | 158 | 1963 | 17.9 | 100 | 19.1 | 24.3 | 23.6 | 3.0 | 3.7 | 12.4 |
| 2 | 253 | 2274 | 38.0 | 87 | 26.0 | 24.0 | 20.3 | 1.4 | 1.8 | 14.8 |
| 3 | 281 | 2361 | 48.4 | 80 | 19.2 | 15.0 | 12.3 | 0.8 | 0.8 | 8.9 |
| 4 | 315 | 2466 | 49.8 | 78 | 20.7 | 15.3 | 12.7 | 0.8 | — | 7.8 |
| 5 | 368 | 2619 | 56.3 | 73 | 21.7 | 14.7 | 11.2 | 0.4 | 0.5 | 5.7 |
| 6 | 433 | 2791 | 58.6 | 76 | 24.2 | 17.0 | 11.5 | 0.6 | 0.5 | 4.9 |
| 7 | 476 | 2895 | 60.1 | — | — | — | — | — | — | — |
| 8 | 492 | 2931 | 61.9 | — | — | — | — | — | — | — |

$T_i$ = Inlet Temperature (°C.)
$T_{ac}$ = Temperature of Adiabatic Compression (°C.)
Conv = Methane Conversion
MB = Total Gaseous Product Recovery

What is claimed is:

1. A process for thermally converting methane to gaseous hydrocarbons comprising:
   compressing and expanding methane and an inert gas in a single cycle of less than one second, the inert gas having a heat capacity ratio, Cp/Cv, greater than that of methane, and being present in an amount sufficient to provide a temperature of adiabatic compression of from about 900° C. to 3000° C., whereby methane is thermally converted to gaseous hydrocarbons which are rapidly cooled to a lower temperature during expansion, thereby substantially preventing thermal conversion of the gaseous hydrocarbons; and,
   recovering the gaseous hydrocarbons.

2. The process of claim 1 wherein the methane and inert gas are compressed in a positive displacement type engine at ratios of from about 2:1 to about 1000:1.

3. The process of claim 2 wherein the methane and inert gas are preheated to temperatures in the range of from 100° C. to 1000° C.

4. The process of claim 1 wherein the inert gas is present in an amount sufficient to provide a temperature of adiabatic compression of from about 1200° C. to about 2700° C.

5. The process of claim 4 wherein the methane and inert gas are preheated to temperatures in the range of from about 300° C. to about 700° C. and then compressed in a positive displacement type engine at ratios of from about 5:1 to about 50:1.

6. The process of claim 5 wherein the compressing and expanding is conducted from about 0.1 to about 0.0001 seconds.

7. A continuous process for thermally converting methane to gaseous hydrocarbons comprising:
   feeding methane and an inert gas having a heat capacity ratio, Cp/Cv, greater than that of methane, to a positive displacement type machine having a reaction chamber and means for rapidly compressing and expanding the reaction chamber at a rate greater than about 60 compression and expansion cycles per minute;
   operating the machine to provide greater than 60 compression and expansion cycles per minute;
   admitting a volume of the gas fed to the machine into the reaction chamber, the volume of gas admitted containing sufficient inert gas to provide, upon compression, a temperature of adiabatic compression of from about 900° C. to about 3000° C.;
   compressing the volume of gas admitted, whereby methane is substantially thermally converted to gaseous hydrocarbons;
   expanding the compressed gaseous hydrocarbons, whereby the hydrocarbons are cooled, thereby substantially preventing thermal cracking thereof;
   evacuating the chamber; and
   continuously repeating the admitting, compressing, expanding and evacuation, whereby methane is continuously thermally converted to gaseous hydrocarbons.

8. The process of claim 7 wherein the amount of inert gas is sufficient to provide a temperature of adiabatic compression of from about 1200° C. to about 2700° C.

9. The process of claim 8 wherein the methane and inert gas are compressed in a positive displacement type engine at ratios of from about 5:1 to about 50:1.

10. The process of claim 9 wherein the methane and inert gas are preheated to temperatures in the range of from 300° C. to 700° C.

* * * * *